United States Patent [19]

Judat et al.

[11] Patent Number: 4,489,210

[45] Date of Patent: Dec. 18, 1984

[54] PROCESS FOR THE HALOGENATION OF ORGANIC COMPOUNDS

[75] Inventors: Helmut Judat, Langenfeld; Ulrich Schnegg, Leverkusen; Karlfried Wedemeyer, Cologne, all of Fed. Rep. of Germany

[73] Assignee: Bayer Aktiengesellschaft, Leverkusen, Fed. Rep. of Germany

[21] Appl. No.: 403,399

[22] Filed: Jul. 30, 1982

[30] Foreign Application Priority Data

Aug. 19, 1981 [DE] Fed. Rep. of Germany ....... 3132692

[51] Int. Cl.$^3$ .............................................. C07C 39/24
[52] U.S. Cl. .................................... 568/779; 560/219; 562/586; 568/348; 568/592; 568/602; 570/196; 570/252
[58] Field of Search ............... 568/779, 774, 348, 602; 570/196, 206, 252, 258; 424/304; 562/586; 560/219

[56] References Cited

U.S. PATENT DOCUMENTS

| | | | |
|---|---|---|---|
| 2,494,993 | 6/1950 | Foster | 568/779 |
| 2,659,759 | 11/1953 | Zemba | 568/779 |
| 4,160,114 | 7/1979 | Shelton et al. | 568/779 |
| 4,237,321 | 12/1980 | Cuthbertson | 568/779 |
| 4,245,127 | 1/1981 | Matsumato et al. | 568/779 |

FOREIGN PATENT DOCUMENTS

| | | | |
|---|---|---|---|
| 0027734 | 3/1977 | Japan | 568/779 |
| 201360 | 10/1967 | U.S.S.R. | 568/779 |

OTHER PUBLICATIONS

Houben-Weyl, "Methoden dee Organsichen Chemie, vol. v/3, p. 516, (1962).

Primary Examiner—Werren B. Lone
Attorney, Agent, or Firm—Sprung, Horn, Kramer & Woods

[57] ABSTRACT

The invention relates to a process for the halogenation of organic compounds in the liquid phase using gaseous halogenating agents, the gaseous halogenating agents being metered into the reaction vessel at such an entry velocity that a gas jet is formed in the reaction mixture at the point of entry of the halogenating agent and the formation of individual gas bubbles at the point of entry is prevented.

14 Claims, No Drawings

PROCESS FOR THE HALOGENATION OF ORGANIC COMPOUNDS

The invention relates to a process for the halogenation of organic compounds in the liquid phase using gaseous halogenating agents.

The halogenation of organic compounds in the liquid phase using gaseous halogenating agents, such as chlorine or bromine, has been known for a long time (compare, for example, Houben-Weyl, Methoden der organischen Chemie ("Methods of Organic Chemistry"), Volume V/3, page 516 (1962)).

It is also known that the selectivity of conversion between first and second halogenation depends on the size of the bubbles of the gaseous halogenation agent employed, insofar as rapid reactions which take place at the interface between the gas phase and the liquid phase, are concerned. Thus, it is known from J. Chem. Eng. (Japan), Volume 3, No. 1, pages 79 et seq. (1970), that, in the chlorination of p-cresol, the selectivity relationship is a question of the mass transfer of material in the phase-boundary layer. It was found in this case that the selectivity in respect of monochlorination can be improved if the diameter of the bubbles of the gaseous chlorinating agent added is increased. The best result, in respect of selectivity, is achieved with large gas bubbles having a diameter of more than 2.5 mm.

It has now been found that the selectivity in the halogenation of organic compounds can be further improved appreciably if the halogenation of organic compounds in which polyhalogenation is possible and which exhibit a difference in the selectivity of conversion in respect of first and second dihalogenation when they are reacted with gaseous halogenating agents, if the latter are introduced into the reaction mixture in the form of gas bubbles having an average diameter of about 3 mm and an average diameter of about 1 mm, is effected by metering the gaseous halogenating agent into the reaction vessel at such an entry velocity that a gas jet is formed in the reaction mixture at the point of entry of the halogenating agent and the formation of individual gas bubbles at the point of entry is prevented.

It has been found that, when the gaseous halogenating agent is introduced into the reaction vessel, a gas jet is formed in the reaction mixture and the formation of individual gas bubbles at the point of entry of the halogenating agent is prevented if the velocity of the gaseous halogenating agent at the point of entry is greater than 7 m/second. The selectivity can be improved further by increasing the entry velocity. In practice, an upper limit for the entry velocity of the gaseous halogenating agent is established by technical factors, for example by the inlet pressure required to produce a high entry velocity. A reasonable compromise between technical outlay and improvement in selectivity is ensured if the entry velocity of the gaseous halogenating agent is within the range from about 9 to 100 m/second, preferably 15 to 50 m/second.

The process according to the invention can be applied in an advantageous manner in the case of organic compounds in which polyhalogenation is possible and which exhibit a difference in the selectivity of conversion in respect of first and second halogenation when they are reacted with gaseous halogenating agents. In order to detect a difference in selectivity of conversion in a polyhalogenation reaction of an organic compound, the procedure followed is, for example, to introduce the halogenating agent into the reaction mixture, first in the form of gas bubbles having an average diameter of about 3 mm and then in the form of gas bubbles having an average diameter of about 1 mm, under otherwise identical reaction conditions. If an improvement in the selectivity of conversion in respect of monohalogenation is achieved when carrying out the halogenation with gas bubbles having an average diameter of about 3 mm, the organic compounds employed in the reaction are then suitable for the process according to the invention. This means that, if these organic compounds are halogenated by the process according to the invention, a further considerable improvement in the selectivity of conversion and thus an improvement in the yield in respect of the monohalogenation product can be achieved. For example, in this case the yield of monohalogen compound is increased if the starting material is an organic compound which has not yet been halogenated. In the case of the organic compounds which are particularly suitable for the process according to the invention, the halogenation rates of the first and second halogenation or polyhalogenation reactions are so high that these reactions take place in the boundary layer next to the liquid. This means that the stationary concentration of the halogenating agent in the reaction mixture is very low and is generally less than 1% by weight, preferably less than 0.05 to 0.1% by weight, relative to the reaction mixture. The organic compounds employed can be aliphatic as well as aromatic hydrocarbons and substituted hydrocarbons which are capable of polyhalogenation and exhibit a difference in the selectivity as mentioned above, such as hydroxy-aromatic compounds, amino-aromatic compounds, alkyl-aromatic compounds, aryl-aromatic compounds, alkoxy-aromatic or aryl-aromatic compounds, ketones, esters, nitriles and dienes and polyenes.

The organic compounds can be employed in the process according to the invention either undiluted or dissolved or dispersed in an inert organic solvent and/or diluent. The following are examples of suitable inert organic solvents and/or diluents: carbon tetrachloride, methylene chloride, dichloroethane, trichloroethane, tetrachloroethane, chlorobenzene, acetic acid, dioxane, dimethylformamide and/or water, preferably carbon tetrachloride, dichloroethane, tetrachloroethane and/or acetic acid.

The quantity of solvent and/or diluent can vary within wide ranges and depends above all on the solubility of the organic compound to be halogenated in the appropriate solvent and on the space/time yield desired. The most advantageous quantity of solvent and/or diluent in a particular case can readily be determined by preliminary tests.

Halogenating agents which can be employed in the process according to the invention are chlorine, bromine or iodine, preferably chlorine or bromine and particularly preferably chlorine. In the process, the halogenating agents are introduced in the form of gas into the reaction mixture in the manner described above. The quantity of halogenating agent employed depends on the desired degree of conversion of the organic compounds employed, and can readily be determined by preliminary tests. For example, in the case of rapid reactions, maximum yields of monohalogen compound are obtained if about 1.0 mol of halogenating agent is employed per mol of organic compound. However, it can also be appropriate to employ less than 1 mol of halogenating agent, for example 0.6 to 0.9 mol of halogenating agent, per mol of organic compound, and to recycle the starting material which has not yet reacted to the halogenation process. However, it is also possible to employ more than 1 mol of halogenating agent, for example 1.1 to 1.4 mols, per mol of organic compound.

The halogenating agent can also be employed in the process according to the invention as a mixture with other inert gases, such as nitrogen, carbon dioxide, noble gases, such as helium or argon, and/or hydrogen halides, such as hydrogen chloride or hydrogen bromide, and/or vapours, such as water vapour and/or solvent vapours, such as methylene chloride vapour.

The temperatures can vary within wide ranges, a lower and an upper limit being set to the reaction temperature by the fact that at very low temperatures the reaction rates of the halogenation reactions become too slow in comparison with the mass transfer and it is therefore no longer possible to achieve an improvement in the selectivity, and, at very high temperatures, a liquid phase can no longer be maintained. The most advantageous reaction temperature can, however, be determined readily by means of simple preliminary tests. In general, the halogenation according to the invention is carried out at about 0° to 150° C., preferably at 40° to 100° C.

The process according to the invention can be carried out under normal pressure, reduced pressure or excess pressure, as required. The process is preferably carried out under normal pressure.

The introduction of the halogenating agent into the reaction mixture can be effected by means of the customary devices for introducing gases. For example, it is possible to effect the introduction of the halogenating agent with the aid of a pipe, a perforated diaphragm or a gas delivery ring which is provided with several small drilled holes.

The process according to the invention can be carried out either continuously or discontinuously.

A possible means of carrying out the process according to the invention on an industrial scale is illustrated below with reference to the chlorination of phenol.

Chlorine is metered into a bubble-cap column equipped with a reflux condenser at an entry velocity of 15 to 25 m/second, through an inlet tube, the end of which is drawn out to form a point, into a solution of phenol in carbon tetrachloride which has been previously placed in the bubble-cap column. When the quantity of chlorine corresponding to the desired degree of conversion has been introduced, the carbon tetrachloride is removed by distillation and the residue is worked up in a known manner by fractional distillation.

In accordance with another process variant (continuous process), the solution of phenol in carbon tetrachloride and the chloride are, for example, metered simultaneously in the ratio corresponding to the desired degree of conversion into a single-stage bubble-cap column. The entry velocity of the chlorine gas is approx. 20 m/second. In the course of this, the reaction mixture is heated to the boil by the heat liberated in the reaction. The heat is removed by evaporative cooling caused by the refluxing solvent. The mixture of products, which flows straight out of the reactor into a distillation column, is freed from the solvent by distillation. A mixture of chlorophenols remains as residue. The exit gas formed in the reaction, which consists mainly of hydrogen chloride, is also passed into the distillation column and is freed there from high-boiling organic products adhering to it. The exit gas which then escapes from the distillation column and which, in addition to hydrogen chloride, contains, almost without exception, only the quantity of carbon tetrachloride corresponding to its vapour pressure, is washed with water in an adiabatically-operating washer, whereby a very pure hydrochloric acid is produced in the sump of the washer; this acid can be employed in a direct manner in this form for further reactions and thus leads to no problems of waste disposal. The crude mixture of chlorophenols is worked up by vacuum distillation into the pure components in a known manner.

The process according to the invention makes it possible to improve appreciably the selectivity of conversion of halogenation reactions which take place in the gas/liquid phase. The high degree of selectivity at which the halogenation reaction takes place also leads to a number of further advantages, such as, say, a higher yield in respect of the monohalogenation product, less undesirable by-products, which is associated with a reduced incidence of costs in the removal of the by-products, and the possibility of carrying out halogenation reactions at higher temperatures, as a result of which it becomes possible to remove the heat of reaction more simply by means of cooling water instead of cooling by brine, which is expensive. In addition, the halogenation reaction can be carried out in a considerably more concentrated solution without the production of more by-products in comparison with the conventional process. As a result, a markedly better space/time yield can be achieved, which is an important factor in considering the profitability of an industrial plant.

A particularly surprising feature of the process according to the invention is that the said advantages are achieved by completely preventing the formation of bubbles when the gaseous halogenating agent is introduced into the reaction mixture, although, according to the state of the art (compare, for example, J. Chem. Eng. (Japan), Volume 3, No. 1, pages 79 et seq. (1970)), the selectivity of the conversion in the halogenation of organic compounds in which polyhalogenation is possible, is raised when the diameter of the bubbles of halogenating agent introduced in the form of gas is increased.

Some of the halogenated organic compounds which can be prepared by the process according to the invention are used as end products, but the majority of them are used as intermediate products, for example for plant protection agents, pharmaceuticals and dyestuffs.

The examples which follow are intended to illustrate the process according to the invention.

EXAMPLE 1 (COMPARISON EXAMPLE)

600 ml of a 4.66-molar solution of m-cresol in 1,2-dichloroethane are brought to a temperature of 50° C. in a bubble-cap column by applying external heat, and 179 g of chlorine gas are passed in at this temperature in the course of approx. 3 hours via a frit D 1 (pore size 100–160 μm) at the base of the bubble-cap column (average bubble size less than 1 mm). The reaction mixture is then cooled and subjected to investigation by gas chromatography (100% method; see Rudolf Kaiser, Chromatographie in der Gasphase ("Chromatography in the Gas Phase"); Volume 4, Quantitative Evaluation, 2nd Part, page 208; B) Hochschultaschenbücher (University Handbooks), Mannheim/Zurich 1969).

The mixture obtained has the following composition:

| | |
|---|---|
| 3-hydroxytoluene | 28.1% |
| 4-chloro-3-hydroxytoluene | 21.2% |
| 6-chloro-3-hydroxytoluene | 35.3% |
| 4,6-dichloro-3-hydroxytoluene | 13.6% |
| Remainder: unidentified products | |

EXAMPLE 2 (COMPARISON EXAMPLE)

Example 1 is repeated, but the frit D 1 is replaced by a tube of diameter 5 mm. The average diameter of the chlorine bubbles is thus greater than 3 mm. Analysis of the crude product by gas chromatography gives the following result:

| | |
|---|---|
| 3-hydroxytoluene | 19.7% |
| 4-chloro-3-hydroxytoluene | 28.3% |
| 6-chloro-3-hydroxytoluene | 46.4% |
| 4,6-dichloro-3-hydroxytoluene | 4.6% |
| Remainder: unidentified products | |

EXAMPLE 3

Example 1 is repeated, but the frit D 1 is replaced by a tube which is drawn out to a point of diameter 0.8 mm. The entry velocity of the chlorine gas is approx. 20 m/second. Analysis by gas chromatography of the mixture of products after gas has been passed in for 1.5 hours gives the following result:

| | |
|---|---|
| 3-hydroxytoluene | 13.0% |
| 4-chloro-3-hydroxytoluene | 29.1% |
| 6-chloro-3-hydroxytoluene | 53.0% |
| 4,6-dichloro-3-hydroxytoluene | 3.6% |
| Remainder: unidentified products | |

The improvement in the selectivity of conversion caused by the new process becomes particularly clear in the following ratios of non-chlorinated material to monochlorinated and dichlorinated material:
0.50:1.00:0.25 in Example 1
0.26:1.00:0.06 in Example 2
0.16:1.00:0.04 in Example 3.

EXAMPLE 4 (COMPARISON EXAMPLE )

Example 1 is repeated, but a 4.23-molar solution off phenol in carbon tetrachloride is employed instead of a 4.66-molar solution of m-cresol in dichloroethane.

After 200 g of chlorine (gas bubbles having an average diameter of less than 1 mm) have been introduced, a crude mixture is obtained, which has the following composition according to analysis by gas chromatography:

| | |
|---|---|
| phenol | 11.8% |
| 2-chlorophenol | 34.3% |
| 4-chlorophenol | 37.1% |
| 2,4-dichlorophenol | 15.0% |
| 2,6-dichlorophenol | 1.1% |
| Remainder: unidentified products | |

EXAMPLE 5 (COMPARISON EXAMPLE)

Example 2 is repeated, but, here again, the m-cresol solution is replaced by the phenol solution. The following result is obtained:

| | |
|---|---|
| phenol | 6.8% |
| 2-chlorophenol | 44.1% |
| 4-chlorophenol | 42.9% |
| 2,4-dichlorophenol | 5.5% |
| 2,6-dichlorophenol | 0.4% |
| Remainder: unidentified products | |

EXAMPLE 6

Example 3 is repeated, using the phenol solution of Example 4. The following result is obtained:

| | |
|---|---|
| phenol | 8.5% |
| 2-chlorophenol | 42.4% |
| 4-chlorophenol | 46.6% |
| 2,4-dichlorophenol | 2.1% |
| 2,6-dichlorophenol | 0.1% |
| Remainder: unidentified products | |

In comparison with Examples 4 and 5, Example 6 shows a considerable decrease in dichlorophenols.

EXAMPLES 7 to 11

Examples 1 to 3 are repeated, but a 4.66-molar solution of p-cresol in carbon tetrachloride is employed instead of the m-cresol solution, and the temperature in Examples 10 (carried out analogously to Example 2) and 11 (carried out analogously to Example 3) is kept at 20° C. The composition of the crude products obtained is shown in the following table.

TABLE
Composition of the crude products from Examples 7 to 11, quoted in % by weight:

| Example | 7* | 8** | 9*** | 10** | 11*** |
|---|---|---|---|---|---|
| 4-hydroxytoluene | 7.4 | 5.9 | 5.3 | 9.8 | 7.4 |
| 3-chloro-4-hydroxytoluene | 77.5 | 82.0 | 87.1 | 79.7 | 82.8 |
| 3,5-dichloro-4-hydroxytoluene | 6.3 | 3.2 | 0.9 | 1.6 | 0.5 |
| Remainder: unidentified products | | | | | |

*analogously to Example 1 (Comparison Example)
**analogously to Example 2 (Comparison Example)
***analogously to Example 3

Once again, the improvement in the selectivity of conversion caused by the new process becomes particularly clear in the following ratios of non-chlorinated material to monochlorinated and dichlorinated material:
0.10:1:0.08 in Example 7
0.07:1:0.04 in Example 8
0.06:1:0.01 in Example 9
0.12:1:0.02 in Example 10
0.09:1:0.01 in Example 11.

EXAMPLES 12 to 14

Examples 1 to 3 are repeated, but m-xylene is employed without a solvent, instead of the solution of m-cresol, 2.6% by weight of $FeCl_3$ are added as a catalyst, and chlorination is carried out at 70° C. The composition of the crude products obtained after introducing 90 mol % of chlorine is shown in the following table.

TABLE

Composition of the crude products from Examples 12 to 14, quoted in % by weight:

| Example | 12* | 13** | 14*** |
|---|---|---|---|
| m-xylene | 31.6 | 27.2 | 23.6 |
| 4-chloro-m-xylene | 43.4 | 56.8 | 63.7 |
| 4,6-dichloro-m-xylene | 14.0 | 11.6 | 10.7 |
| Remainder: unidentified products | | | |

*analogous to Example 1 (Comparison Example)
** analogous to Example 2 (Comparison Example)
***analogous to Example 3.

EXAMPLE 15

1,000 ml per hour of a 33% strength by weight solution of phenol in carbon tetrachloride are pumped, via a dip tube, into a bubble-cap column of capacity 2 l, equipped with a reflux condenser, a gas inlet nozzle (1.5 mm diameter), a gas outlet tube, a dip tube and an overflow tube. 360 g per hour of chlorine are introduced via the gas inlet nozzle while the mixture boils under reflux (the entry velocity of the chloride is approx. 18 m/second). A stream of crude chlorophenol, dissolved in carbon tetrachloride, leaves the bubble-cap column continuously via the overflow tube. The crude solution flows directly into the centre of a silver-jacketed column 1 1.5 m long, which is filled with packing. The exit gas is freed from the bulk of the carbon tetrachloride via the water-cooled reflux condenser and is then also fed into the column. 620 g per hour of crude chlorophenol are obtained in the sump of the column, while 873 g of carbon tetrachloride are separated from the exit gas at the head of the column via a cooling system using brine cooling. According to analysis by gas chromatography, the crude mixture of chlorophenols contains the following:

| | |
|---|---|
| phenol | 5.3% |
| 2-chlorophenol | 40.4% |
| 4-chlorophenol | 39.8% |
| 2,4-dichlorophenol | 13.6% |
| 2,6-dichlorophenol | 0.9% |
| Remainder: unidentified products | |

The cooled exit gas is passed to an adiabatic washer in which 420 g per hour of water flow counter-current to the gas mixture in a glass packed column 1.5 m high. A mixture consisting of entrained water and 15 g/hour of carbon tetrachloride is taken off at the head of the column. 600 g/hour of 30% strength by weight hydrochloric acid, which has a total carbon content (organically bound carbon plus inorganic carbon) of 6 ppm, is withdrawn from the sump of the column.

What is claimed is:

1. A process for the halogenation of an organic compound which
   (1) is polyhalogenatable
   (2) is halogenated with a gaseous halogenating agent to form more mono halogenated organic compound when halogenated with gas bubbles of 3 mm in diameter than is formed when said gas bubble has a diameter of 1 mm in the liquid phase which comprises feeding said gaseous halogenating agent to a liquid phase containing said organic compound at a temperature of 0° to 150° C. in the form of a gas jet at the point said halogenating agent enters the reaction vessel whereby the formation of bubbles is prevented, said halogenating agent being chlorine, bromine or iodine.

2. A process according to claim 1, wherein said gaseous halogenating agent is introduced into the reaction vessel at an entry velocity greater than 7 meters per second.

3. A process according to claim 1, wherein said gaseous halogenating agent is introduced into the reaction vessel at an entry velocity of 9 to 100 meters per second.

4. A process according to claim 1, wherein said gaseous halogenating agent is introduced into said reaction vessel at an entry velocity of 15 to 50 meters per second.

5. A process according to claim 1, wherein said halogenating agent is chlorine.

6. A process according to claim 1, wherein said halogenating agent is in admixture with an inert gas or vapor.

7. A process according to claim 6, wherein said inert gas or vapor is nitrogen, carbon dioxide, helium, argon, hydrogen chloride, hydrogen bromide, water vapor, methylene chloride vapor or a mixture thereof.

8. A process according to claim 1, wherein the process is carried out at a temperature of 10° to 100° C.

9. A process according to claim 1 wherein said organic compound is a hydroxy aromatic compound, an amino aromatic compound, an alkyl aromatic compound, an aryl aromatic compound, an alkoxy aromatic compound, a ketone, ester, nitrile, diene or polyene.

10. A process according to claim 1 wherein said organic compound is of the group consisting of phenol, m-cresol, 3-hydroxytoluene, p-cresol and m-xylene.

11. A process according to claim 1 wherein said organic compound is m-cresol.

12. A process according to claim 1 wherein said organic compound is phenol.

13. A process according to claim 1 wherein said organic compound is p-cresol.

14. A process according to claim 1 wherein said organic compound is m-xylene.

* * * * *